(12) United States Patent
Yu

(10) Patent No.: US 7,291,768 B2
(45) Date of Patent: Nov. 6, 2007

(54) PLANT MYB PROTEINS

(75) Inventor: Su-May Yu, Taipei (TW)

(73) Assignee: Academia Sinica (TW)

( * ) Notice: Subject to any disclaimer, the term of this patent is extended or adjusted under 35 U.S.C. 154(b) by 101 days.

(21) Appl. No.: 10/630,636

(22) Filed: Jul. 30, 2003

(65) Prior Publication Data

US 2004/0107456 A1 Jun. 3, 2004

Related U.S. Application Data

(60) Provisional application No. 60/399,999, filed on Jul. 31, 2002.

(51) Int. Cl.
*C12N 15/29* (2006.01)
*C12N 15/82* (2006.01)
*C12N 15/87* (2006.01)
*A01H 5/00* (2006.01)

(52) U.S. Cl. .................. 800/298; 536/23.6; 435/410; 800/320.1; 800/278; 800/320; 800/320.2

(58) Field of Classification Search ............. 536/23.1, 536/23.6, 24.1; 435/410, 419, 468; 800/298, 800/278, 287, 320.2
See application file for complete search history.

(56) References Cited

U.S. PATENT DOCUMENTS 5,460,952 A   10/1995 Yu et al.
5,677,474 A   10/1997 Rogers
5,693,506 A   12/1997 Rodriguez
5,712,112 A    1/1998 Yu et al.
5,888,789 A    3/1999 Rodriguez
5,917,029 A    6/1999 Yu
5,939,601 A *  8/1999 Klessig et al. ............. 800/279

OTHER PUBLICATIONS

Schwechheimer et al (2000, Funct Intergr Genomics 1:35-43).*
Fourgoux-Nicol et al (1999, Plant Molecular Biology 40 :857-872).*
Bowie et al, Science 247:1306-1310, 1990.*
McConnell et al, Nature 411 (6838):709-713, 2001.*
Dong et al (Nov. 2001, NCBI Accession No. BM038003).*
Chung-An Lu et al. "Sugar Response Sequence In The Promoter Of A Rice α-Amylase Gene Serves As A Transcriptional Enhancer". The Journal of Biological Chemistry 273(17):10120-10130, 1998.

* cited by examiner

*Primary Examiner*—Stuart F. Baum
(74) *Attorney, Agent, or Firm*—Fish & Richardson P.C.

(57) ABSTRACT

A pure polypeptide containing an amino acid sequence at least 70% identical to SEQ ID NO:7, 8, or 9. The polypeptide regulates expression of a gene in a cell. Also disclosed is an isolated nucleic acid characterized in that it hybridizes under stringent conditions to SEQ ID NO:1, 2, or 3, or a complementary sequence thereof. Also within the scope of the invention are a transformed cell or a transgenic plant containing such a nucleic acid and a method of identifying a compound that modulates the activity of the polypeptide.

11 Claims, No Drawings

SEQUENCE LISTING

<160> NUMBER OF SEQ ID NOS: 21

<210> SEQ ID NO 1
<211> LENGTH: 1330
<212> TYPE: DNA
<213> ORGANISM: Oryza sativa (japonica cultivar-group)
<220> FEATURE:
<221> NAME/KEY: CDS
<222> LOCATION: (20)...(937)

<400> SEQUENCE: 1

```
gtgcgagatc caccacccg atg acc tcc cag gcg gcg acg acg acg acc acg      52
                    Met Thr Ser Gln Ala Ala Thr Thr Thr Thr Thr
                     1               5                  10 gcg gcg gcg gcg gcg gcg tgg acc agg gag gac gac aag gcg ttc gag     100
Ala Ala Ala Ala Ala Ala Trp Thr Arg Glu Asp Asp Lys Ala Phe Glu
                15                  20                  25 aac gcg ctc gcg gct tgc gcg gcg ccg ccg ccc gcg gac gga ggc gcg     148
Asn Ala Leu Ala Ala Cys Ala Ala Pro Pro Pro Ala Asp Gly Gly Ala
        30                  35                  40 ccc gac gac gac tgg ttc gcc gcg ctc gcc gcg agc gtg ccc ggg gcg     196
Pro Asp Asp Asp Trp Phe Ala Ala Leu Ala Ala Ser Val Pro Gly Ala
    45                  50                  55 agg tcg gcg gag gag gtg cgg agg cac tac gag gcg ctg gtg gag gac     244
Arg Ser Ala Glu Glu Val Arg Arg His Tyr Glu Ala Leu Val Glu Asp
60                  65                  70                  75 gtc gcg gcc atc gac gcg ggc cgc gtc ccg ctc ccg cgc tac gcc ggg     292
Val Ala Ala Ile Asp Ala Gly Arg Val Pro Leu Pro Arg Tyr Ala Gly
                80                  85                  90 gag gag tcc gcg gcg ccg ccc gac gga gcc gga gcc gcc gcc gcc gcg     340
Glu Glu Ser Ala Ala Pro Pro Asp Gly Ala Gly Ala Ala Ala Ala Ala
                95                 100                 105 tcc aag gac ggc gga cac cgg cgc gac gag cgc aag ggc ggc ggc ggc     388
Ser Lys Asp Gly Gly His Arg Arg Asp Glu Arg Lys Gly Gly Gly Gly
           110                 115                 120 ggg tac gac ggc ggc aag agc tgc tcc aag gcg gag cag gag agg cgc     436
Gly Tyr Asp Gly Gly Lys Ser Cys Ser Lys Ala Glu Gln Glu Arg Arg
       125                 130                 135 aag ggc atc cca tgg acg gag gaa gag cac agg ctg ttc ttg ctg ggg     484
Lys Gly Ile Pro Trp Thr Glu Glu Glu His Arg Leu Phe Leu Leu Gly
```

-continued

```
              140                 145                 150                 155
ctg gac aag ttc ggc aag ggg gac tgg cgg agc atc tcg cgc aac ttc         532
Leu Asp Lys Phe Gly Lys Gly Asp Trp Arg Ser Ile Ser Arg Asn Phe
                        160                 165                 170 gtc atc tcg cgg acg cca acg cag gtg gcg agc cac gcg cag aag tac         580
Val Ile Ser Arg Thr Pro Thr Gln Val Ala Ser His Ala Gln Lys Tyr
                175                 180                 185 ttc atc cgc ctc aac tcc atg aac cgc gac cgc cgc cgc tcc agc atc         628
Phe Ile Arg Leu Asn Ser Met Asn Arg Asp Arg Arg Arg Ser Ser Ile
                    190                 195                 200 cac gac atc acc agc gtc acc gcc ggc gat cag gtc gcc gcg cag cag         676
His Asp Ile Thr Ser Val Thr Ala Gly Asp Gln Val Ala Ala Gln Gln
            205                 210                 215 ggc gcc ccg atc acc ggc cac cag gcc acg ggc aac ccc gcg gcg gcg         724
Gly Ala Pro Ile Thr Gly His Gln Ala Thr Gly Asn Pro Ala Ala Ala
220                 225                 230                 235 gcg ctg ggc ccg ccg ggc atg aag cac cac cac cac cac cac ccg ggc         772
Ala Leu Gly Pro Pro Gly Met Lys His His His His His His Pro Gly
                        240                 245                 250 ggc gcg ccg ccg ccc atg ccc atg tac agc gcc gcg ccc atg ggc cac         820
Gly Ala Pro Pro Pro Met Pro Met Tyr Ser Ala Ala Pro Met Gly His
                255                 260                 265 ccc gtc gcc ggc cac atg gtg ccc gcc gcc gtc ggc acg ccg gtg gtg         868
Pro Val Ala Gly His Met Val Pro Ala Ala Val Gly Thr Pro Val Val
                    270                 275                 280 ttc ccg ccg ggc cac gcg ccg tac gtc gtg ccc gtc ggc tac ccg gcg         916
Phe Pro Pro Gly His Ala Pro Tyr Val Val Pro Val Gly Tyr Pro Ala
            285                 290                 295 cct ccg gcc aag atg cac caa tgacgcgcca tggacggaca tgagcagcat           967
Pro Pro Ala Lys Met His Gln
300                 305 ttcttcctcc tcctttcttg atgtcaatct tgatttgttc tttgtgtagt cgccggctca     1027
tcgtccctga tcatcttgtt cttctcacaa tctcactaat gtaaacatac atagatcaga     1087
tgccaagagt gcagggattg gggattaaag gcgaataagt aaagtatttt gctgactgtt     1147
tgcaagtgat catcacgtac acccggtgaa agcttagctc caaatgtgga tgtaattagc     1207
agcggccttc cgtacgtggt ggcgccgatc gatgatcttg caggggttgc aattagggat     1267
tgatttccat tttgctgatg taaatttgcc aactgtctca ttggaccaaa aaaaaaaaaa     1327
aaa                                                                   1330

<210> SEQ ID NO 2
<211> LENGTH: 1012
<212> TYPE: DNA
<213> ORGANISM: Oryza sativa (japonica cultivar-group)
<220> FEATURE:
<221> NAME/KEY: CDS
<222> LOCATION: (92)...(919)

<400> SEQUENCE: 2
cgaggtccgc ggcggcggcg gcggagttga cgaggaggag tacgaggagg aggaggtgga      60
gggtggattg ttcatcaaga agagctccag t atg ccc aac ctc acc tcc atc         112
                                   Met Pro Asn Leu Thr Ser Ile
                                    1               5 gac ccg ctg ccg gtg ccg gcc gac ggc ggc aaa cgg cgc gcc tcc gac         160
Asp Pro Leu Pro Val Pro Ala Asp Gly Gly Lys Arg Arg Ala Ser Asp
        10                  15                  20 gac tcc gag ctc gcc tcc ggc cag cag aag cgc cgc cgc cgc aag gtg         208
Asp Ser Glu Leu Ala Ser Gly Gln Gln Lys Arg Arg Arg Arg Lys Val
    25                  30                  35
```

```
cag gag agg aag aaa ggg gta cca tgg act gag gag cac aag aaa    256
Gln Glu Arg Lys Lys Gly Val Pro Trp Thr Glu Glu His Lys Lys
 40              45                  50                  55 ttc ctg gaa ggg ctg agg cag ctg gga aaa ggg gac tgg aga ggc atc   304
Phe Leu Glu Gly Leu Arg Gln Leu Gly Lys Gly Asp Trp Arg Gly Ile
         60                  65                  70 tcc aag aac ttt gtg acc agc agg acg gcg act cag gtg gcc agc cac   352
Ser Lys Asn Phe Val Thr Ser Arg Thr Ala Thr Gln Val Ala Ser His
             75                  80                  85 gcc cag aag tac ttc ctc cgg cag acc aac cct ggc aaa aag aag cgc   400
Ala Gln Lys Tyr Phe Leu Arg Gln Thr Asn Pro Gly Lys Lys Lys Arg
         90                  95                 100 cgg gcc agc ctc ttt gat gtt gtt gct gag tgc agt gat gat caa ctt   448
Arg Ala Ser Leu Phe Asp Val Val Ala Glu Cys Ser Asp Asp Gln Leu
    105                 110                 115 cca agt cct cag agt gtt gga act aag cct cct acc cag gat ata att   496
Pro Ser Pro Gln Ser Val Gly Thr Lys Pro Pro Thr Gln Asp Ile Ile
120                 125                 130                 135 cat aca gat cgc ggc gat gtc ccg ata cta agc tat cca gtt gct aga   544
His Thr Asp Arg Gly Asp Val Pro Ile Leu Ser Tyr Pro Val Ala Arg
                140                 145                 150 ggc ttt aga ggc gat agc gtg cag gtt gat gaa cta act gaa tat gtg   592
Gly Phe Arg Gly Asp Ser Val Gln Val Asp Glu Leu Thr Glu Tyr Val
            155                 160                 165 aag aga tta aag gcc gcc gag gac atg tcg ctc tcc atg atc tct gga   640
Lys Arg Leu Lys Ala Ala Glu Asp Met Ser Leu Ser Met Ile Ser Gly
        170                 175                 180 ctg gaa atg gca tca tca tcc atc agc agt cta gag ctc agt atc gcg   688
Leu Glu Met Ala Ser Ser Ser Ile Ser Ser Leu Glu Leu Ser Ile Ala
    185                 190                 195 ccc tct cat ttg cgg atc gac ggg gcc atc aag ggg ctg gga tcc aaa   736
Pro Ser His Leu Arg Ile Asp Gly Ala Ile Lys Gly Leu Gly Ser Lys
200                 205                 210                 215 ccc aat ttt ccc ccg aag gaa ttt gga tcg gct tca gct act gtt ttt   784
Pro Asn Phe Pro Pro Lys Glu Phe Gly Ser Ala Ser Ala Thr Val Phe
                220                 225                 230 tgt ccc ccc tgt tgt tgt ttg ttg ttg ttg ttt ttt ttt ttt ttt ttt   832
Cys Pro Pro Cys Cys Cys Leu Leu Leu Leu Phe Phe Phe Phe Phe
            235                 240                 245 gcg ggg gtt gtt tgt tgt tgt tgt tgt tgt agt tgt cat gct aac ttt   880
Ala Gly Val Val Cys Cys Cys Cys Cys Ser Cys His Ala Asn Phe
        250                 255                 260 gta ttt ggg tca tgt ggg gtt tct ttc acc agt ttt ata taatacagag   929
Val Phe Gly Ser Cys Gly Val Ser Phe Thr Ser Phe Ile
    265                 270                 275 agaatgtcag tcccttccga gacatgttta aaaaaaaaaa aaaaaaaaaa aaaaaaaaaa    989
aaaaaaaaaa aaaaaaaaaa aaa                                          1012

<210> SEQ ID NO 3
<211> LENGTH: 1287
<212> TYPE: DNA
<213> ORGANISM: Oryza sativa (japonica cultivar-group)
<220> FEATURE:
<221> NAME/KEY: CDS
<222> LOCATION: (67)...(1020)

<400> SEQUENCE: 3
atcgatcgat cgatctccat aggtggggga agggaagctt tggaaggtgg agggacggag     60 gggggg atg acg agg cgg tgc tcg cac tgc agc cac aac ggg cac aac       108
```

|  |  |
|---|---:|
| Met Thr Arg Arg Cys Ser His Cys Ser His Asn Gly His Asn<br>1                      5                    10 | |
| tcg cgg acg tgc ccc aac cgc ggg gtc aag atc ttc ggg gtg cgc ctc<br>Ser Arg Thr Cys Pro Asn Arg Gly Val Lys Ile Phe Gly Val Arg Leu<br>15                    20                    25                    30 | 156 |
| acc gat ggc tcc atc cgc aag agc gcc agc atg ggg aac ctc tcc ctc<br>Thr Asp Gly Ser Ile Arg Lys Ser Ala Ser Met Gly Asn Leu Ser Leu<br>                    35                    40                    45 | 204 |
| ctc tcc tcc gcc gcc gga tcc acc agc ggc ggc gcc tcc ccc gcc gac<br>Leu Ser Ser Ala Ala Gly Ser Thr Ser Gly Gly Ala Ser Pro Ala Asp<br>                50                    55                    60 | 252 |
| ggc ccc gac gcc gcc ccc acc gcc gcc gac ggc tac gcc tcc gac gac<br>Gly Pro Asp Ala Ala Pro Thr Ala Ala Asp Gly Tyr Ala Ser Asp Asp<br>      65                    70                    75 | 300 |
| ttc gtc cag ggc ttc tcc tcc gcc acc cgc gac cgc aag aag ggt gtt<br>Phe Val Gln Gly Phe Ser Ser Ala Thr Arg Asp Arg Lys Lys Gly Val<br>           80                    85                    90 | 348 |
| cct tgg act gaa gaa gaa cac cgg agg ttt ttg ctt gga ttg caa aag<br>Pro Trp Thr Glu Glu Glu His Arg Arg Phe Leu Gly Leu Gln Lys<br>95                    100                  105               110 | 396 |
| ctt ggc aaa ggt gat tgg cga gga atc tct cgt aat ttc gtg gtc tca<br>Leu Gly Lys Gly Asp Trp Arg Gly Ile Ser Arg Asn Phe Val Val Ser<br>                    115                  120                  125 | 444 |
| aga aca cct act caa gta gcc agt cat gct cag aaa tat ttt ata cgc<br>Arg Thr Pro Thr Gln Val Ala Ser His Ala Gln Lys Tyr Phe Ile Arg<br>                130                      135                  140 | 492 |
| caa tcc aat atg acc aga agg aaa aga agg tct agc ctt ttt gac atg<br>Gln Ser Asn Met Thr Arg Arg Lys Arg Arg Ser Ser Leu Phe Asp Met<br>                    145                  150                 155 | 540 |
| gtg cca gat gag tct atg gac ctt cca cca ctt cct gga ggt caa gaa<br>Val Pro Asp Glu Ser Met Asp Leu Pro Pro Leu Pro Gly Gly Gln Glu<br>            160                      165                  170 | 588 |
| cca gag acc caa gta tta aat caa cca gca cta cct cca ccg aag gag<br>Pro Glu Thr Gln Val Leu Asn Gln Pro Ala Leu Pro Pro Pro Lys Glu<br>175                    180                  185                   190 | 636 |
| gaa gag gag gta gat tct atg gag tca gat act tct gcc gtt gca gag<br>Glu Glu Glu Val Asp Ser Met Glu Ser Asp Thr Ser Ala Val Ala Glu<br>                    195                  200                 205 | 684 |
| agc tct tcc gct tct gct atc atg cca gat aat ttg cag tcg acc tat<br>Ser Ser Ser Ala Ser Ala Ile Met Pro Asp Asn Leu Gln Ser Thr Tyr<br>                210                      215                  220 | 732 |
| cca gtg att gtt cca gct tat ttc tcg ccc ttt ttg caa ttc tcg gtt<br>Pro Val Ile Val Pro Ala Tyr Phe Ser Pro Phe Leu Gln Phe Ser Val<br>                    225                  230                 235 | 780 |
| cct ttc tgg caa aat cag aaa gat gaa gat ggt cct gtg caa gaa aca<br>Pro Phe Trp Gln Asn Gln Lys Asp Glu Asp Gly Pro Val Gln Glu Thr<br>            240                      245                  250 | 828 |
| cat gag att gtc aag cct gtt cca gtt cat tca aag agc cca atc aac<br>His Glu Ile Val Lys Pro Val Pro Val His Ser Lys Ser Pro Ile Asn<br>255                    260                  265                   270 | 876 |
| gtt gat gag ctt gtt ggc atg tcg aag ctc agc ata gga gag tcc aat<br>Val Asp Glu Leu Val Gly Met Ser Lys Leu Ser Ile Gly Glu Ser Asn<br>                    275                  280                 285 | 924 |
| caa gag aca gag tct act tct ctt tca tta aat ctg gta gga ggt caa<br>Gln Glu Thr Glu Ser Thr Ser Leu Ser Leu Asn Leu Val Gly Gly Gln<br>                    290                      295                 300 | 972 |
| aat aga caa tca gct ttc cat gca aat cca cca aca agg gca cag gca<br>Asn Arg Gln Ser Ala Phe His Ala Asn Pro Pro Thr Arg Ala Gln Ala<br>                305                      310                  315 | 1020 |

-continued

| tgatctggtt gtgcacacaa ctgcatttag atgaatccca ggcaaaataa gctttgcctc | 1080 |
| cttgttttt tgttttatt ttaagattaa ccgttctccg tagtctgtat catgtgctgt | 1140 |
| aagttatgct atgtatgaat gtatctgttg tttgtctggc acacatgata aatcactcta | 1200 |
| tgttaacaaa atcagtaatg gtagtgctga tcttcgtggt tgtactgttg taaactcttt | 1260 |
| tataagaaaa aaaaatatta gttagtc | 1287 |

<210> SEQ ID NO 4
<211> LENGTH: 918
<212> TYPE: DNA
<213> ORGANISM: Oryza sativa (japonica cultivar-group)

<400> SEQUENCE: 4

| atgacctccc aggcggcgac gacgacgacc acggcggcgg cggcggcggc gtggaccagg | 60 |
| gaggacgaca aggcgttcga gaacgcgctc gcggcttgcg cggcgccgcc gcccgcggac | 120 |
| ggaggcgcgc ccgacgacga ctggttcgcc gcgctcgccg cgagcgtgcc cggggcgagg | 180 |
| tcggcggagg aggtgcggag gcactacgag gcgctggtgg aggacgtcgc ggccatcgac | 240 |
| gcgggccgcg tcccgctccc gcgctacgcc ggggaggagt ccgcggcgcc gcccgacgga | 300 |
| gccggagccg ccgccgccgc gtccaaggac ggcggacacc ggcgcgacga gcgcaagggc | 360 |
| ggcggcggcg ggtacgacgg cggcaagagc tgctccaagg cggagcagga gaggcgcaag | 420 |
| ggcatcccat ggacggagga agagcacagg ctgttcttgc tggggctgga caagttcggc | 480 |
| aaggggggact gcggagcat ctcgcgcaac ttcgtcatct cgcggacgcc aacgcaggtg | 540 |
| gcgagccacg cgcagaagta cttcatccgc ctcaactcca tgaaccgcga ccgccgccgc | 600 |
| tccagcatcc acgacatcac cagcgtcacc gccggcgatc aggtcgccgc gcagcagggc | 660 |
| gccccgatca ccggccacca ggccacgggc aaccccgcgg cggcggcgct gggcccgccg | 720 |
| ggcatgaagc accaccacca ccaccacccg gcggcgcgc cgccgcccat gcccatgtac | 780 |
| agcgccgcgc ccatgggcca ccccgtcgcc ggccacatgg tgcccgccgc cgtcggcacg | 840 |
| ccggtggtgt tccgccgggg ccacgcgccg tacgtcgtgc ccgtcggcta cccggcgcct | 900 |
| ccggccaaga tgcaccaa | 918 |

<210> SEQ ID NO 5
<211> LENGTH: 828
<212> TYPE: DNA
<213> ORGANISM: Oryza sativa (japonica cultivar-group)

<400> SEQUENCE: 5

| atgcccaacc tcacctccat cgacccgctg ccggtgccgg ccgacggcgg caaacggcgc | 60 |
| gcctccgacg actccgagct cgcctccggc cagcagaagc gccgccgccg caaggtgcag | 120 |
| gagaggaaga aagggtacc atggactgag gaggagcaca agaaattcct ggaagggctg | 180 |
| aggcagctgg ggaaggggga ctggagaggc atctccaaga actttgtgac cagcaggacg | 240 |
| gcgactcagg tggccagcca cgcccagaag tacttcctcc ggcagaccaa ccctggcaaa | 300 |
| aagaagcgcc gggccagcct ctttgatgtt gttgctgagt gcagtgatga tcaacttcca | 360 |
| agtcctcaga gtgttggaac taagcctcct acccaggata taattcatac agatcgcggc | 420 |
| gatgtcccga tactaagcta tccagttgct agaggctta gaggcgatag cgtgcaggtt | 480 |
| gatgaactaa ctgaatatgt gaagagatta aaggccgccg aggacatgtc gctctccatg | 540 |
| atctctggac tggaaatggc atcatcatcc atcagcagtc tagagctcag tatcgcgccc | 600 |
| tctcatttgc ggatcgacgg ggccatcaag gggctgggat ccaaacccaa ttttccccg | 660 |

```
aaggaatttg gatcggcttc agctactgtt ttttgtcccc cctgttgttg tttgttgttg      720
ttgttttttt tttttttttt tgcggggggtt gtttgttgtt gttgttgttg tagttgtcat      780
gctaactttg tatttgggtc atgtggggtt tctttcacca gttttata                  828
```

<210> SEQ ID NO 6
<211> LENGTH: 954
<212> TYPE: DNA
<213> ORGANISM: Oryza sativa (japonica cultivar-group)

<400> SEQUENCE: 6

```
atgacgaggc ggtgctcgca ctgcagccac aacgggcaca actcgcggac gtgccccaac       60
cgcggggtca agatcttcgg ggtgcgcctc accgatggct ccatccgcaa gagcgccagc      120
atggggaacc tctccctcct ctcctccgcc gccggatcca ccagcggcgg cgcctccccc      180
gccgacggcc ccgacgccgc ccccaccgcc gccgacggct acgcctccga cgacttcgtc      240
cagggcttct cctccgccac ccgcgaccgc aagaaggtg ttccttggac tgaagaagaa      300
caccggaggt ttttgcttgg attgcaaaag cttggcaaag gtgattggcg aggaatctct      360
cgtaatttcg tggtctcaag aacacctact caagtagcca gtcatgctca gaaatatttt      420
atacgccaat ccaatatgac cagaaggaaa agaaggtcta gccttttga catggtgcca      480 gatgagtcta tggaccttcc accacttcct ggaggtcaag aaccagagac ccaagtatta      540
aatcaaccag cactacctcc accgaaggag gaagaggagg tagattctat ggagtcagat      600
acttctgccg ttgcagagag ctcttccgct tctgctatca tgccagataa tttgcagtcg      660
acctatccag tgattgttcc agcttatttc tcgcccttt tgcaattctc ggttcctttc      720
tggcaaaatc agaagatga agatggtcct gtgcaagaaa cacatgagat tgtcaagcct      780
gttccagttc attcaaagag cccaatcaac gttgatgagc ttgttggcat gtcgaagctc      840
agcataggag agtccaatca agagacagag tctacttctc tttcattaaa tctggtagga      900
ggtcaaaata gacaatcagc tttccatgca aatccaccaa caagggcaca ggca           954
```

<210> SEQ ID NO 7
<211> LENGTH: 306
<212> TYPE: PRT
<213> ORGANISM: Oryza sativa (japonica cultivar-group)

<400> SEQUENCE: 7

```
Met Thr Ser Gln Ala Ala Thr Thr Thr Thr Ala Ala Ala Ala
  1               5                  10                  15

Ala Trp Thr Arg Glu Asp Asp Lys Ala Phe Glu Asn Ala Leu Ala Ala
                 20                  25                  30

Cys Ala Ala Pro Pro Ala Asp Gly Gly Ala Pro Asp Asp Trp
             35                  40                  45

Phe Ala Ala Leu Ala Ala Ser Val Pro Gly Ala Arg Ser Ala Glu Glu
         50                  55                  60

Val Arg Arg His Tyr Glu Ala Leu Val Glu Asp Val Ala Ala Ile Asp
 65                  70                  75                  80

Ala Gly Arg Val Pro Leu Pro Arg Tyr Ala Gly Glu Glu Ser Ala Ala
                 85                  90                  95

Pro Pro Asp Gly Ala Gly Ala Ala Ala Ala Ser Lys Asp Gly Gly
            100                 105                 110

His Arg Arg Asp Glu Arg Lys Gly Gly Gly Gly Tyr Asp Gly Gly
            115                 120                 125
```

-continued

Lys Ser Cys Ser Lys Ala Glu Gln Glu Arg Arg Lys Gly Ile Pro Trp
130                 135                 140

Thr Glu Glu His Arg Leu Phe Leu Leu Gly Leu Asp Lys Phe Gly
145                 150                 155                 160

Lys Gly Asp Trp Arg Ser Ile Ser Arg Asn Phe Val Ile Ser Arg Thr
                165                 170                 175

Pro Thr Gln Val Ala Ser His Ala Gln Lys Tyr Phe Ile Arg Leu Asn
            180                 185                 190

Ser Met Asn Arg Asp Arg Arg Ser Ser Ile His Asp Ile Thr Ser
        195                 200                 205

Val Thr Ala Gly Asp Gln Val Ala Ala Gln Gln Gly Ala Pro Ile Thr
    210                 215                 220

Gly His Gln Ala Thr Gly Asn Pro Ala Ala Ala Leu Gly Pro Pro
225                 230                 235                 240

Gly Met Lys His His His His His Pro Gly Gly Ala Pro Pro Pro
                245                 250                 255

Met Pro Met Tyr Ser Ala Ala Pro Met Gly His Pro Val Ala Gly His
                260                 265                 270

Met Val Pro Ala Ala Val Gly Thr Pro Val Val Phe Pro Pro Gly His
            275                 280                 285

Ala Pro Tyr Val Val Pro Val Gly Tyr Pro Ala Pro Pro Ala Lys Met
        290                 295                 300

His Gln
305

<210> SEQ ID NO 8
<211> LENGTH: 276
<212> TYPE: PRT
<213> ORGANISM: Oryza sativa (japonica cultivar-group)

<400> SEQUENCE: 8

Met Pro Asn Leu Thr Ser Ile Asp Pro Leu Pro Val Pro Ala Asp Gly
1               5                   10                  15

Gly Lys Arg Arg Ala Ser Asp Asp Ser Glu Leu Ala Ser Gly Gln Gln
            20                  25                  30

Lys Arg Arg Arg Arg Lys Val Gln Glu Arg Lys Lys Gly Val Pro Trp
        35                  40                  45

Thr Glu Glu His Lys Lys Phe Leu Glu Gly Leu Arg Gln Leu Gly
    50                  55                  60

Lys Gly Asp Trp Arg Gly Ile Ser Lys Asn Phe Val Thr Ser Arg Thr
65                  70                  75                  80

Ala Thr Gln Val Ala Ser His Ala Gln Lys Tyr Phe Leu Arg Gln Thr
                85                  90                  95

Asn Pro Gly Lys Lys Arg Arg Ala Ser Leu Phe Asp Val Val Ala
            100                 105                 110

Glu Cys Ser Asp Asp Gln Leu Pro Ser Pro Gln Ser Val Gly Thr Lys
        115                 120                 125

Pro Pro Thr Gln Asp Ile Ile His Thr Asp Arg Gly Asp Val Pro Ile
    130                 135                 140

Leu Ser Tyr Pro Val Ala Arg Gly Phe Arg Gly Asp Ser Val Gln Val
145                 150                 155                 160

Asp Glu Leu Thr Glu Tyr Val Lys Arg Leu Lys Ala Ala Glu Asp Met
                165                 170                 175

Ser Leu Ser Met Ile Ser Gly Leu Glu Met Ala Ser Ser Ser Ile Ser
            180                 185                 190

```
Ser Leu Glu Leu Ser Ile Ala Pro Ser His Leu Arg Ile Asp Gly Ala
            195                 200                 205

Ile Lys Gly Leu Gly Ser Lys Pro Asn Phe Pro Pro Lys Glu Phe Gly
        210                 215                 220

Ser Ala Ser Ala Thr Val Phe Cys Pro Pro Cys Cys Leu Leu Leu
225                 230                 235                 240

Leu Phe Phe Phe Phe Phe Ala Gly Val Val Cys Cys Cys Cys
                245                 250                 255

Cys Ser Cys His Ala Asn Phe Val Phe Gly Ser Cys Gly Val Ser Phe
            260                 265                 270

Thr Ser Phe Ile
        275

<210> SEQ ID NO 9
<211> LENGTH: 318
<212> TYPE: PRT
<213> ORGANISM: Oryza sativa (japonica cultivar-group)

<400> SEQUENCE: 9

Met Thr Arg Arg Cys Ser His Cys Ser His Asn Gly His Asn Ser Arg
1               5                   10                  15

Thr Cys Pro Asn Arg Gly Val Lys Ile Phe Gly Val Arg Leu Thr Asp
            20                  25                  30

Gly Ser Ile Arg Lys Ser Ala Ser Met Gly Asn Leu Ser Leu Leu Ser
        35                  40                  45

Ser Ala Ala Gly Ser Thr Ser Gly Gly Ala Ser Pro Ala Asp Gly Pro
50                  55                  60

Asp Ala Ala Pro Thr Ala Ala Asp Gly Tyr Ala Ser Asp Asp Phe Val
65                  70                  75                  80

Gln Gly Phe Ser Ser Ala Thr Arg Asp Arg Lys Lys Gly Val Pro Trp
                85                  90                  95

Thr Glu Glu Glu His Arg Arg Phe Leu Leu Gly Leu Gln Lys Leu Gly
            100                 105                 110

Lys Gly Asp Trp Arg Gly Ile Ser Arg Asn Phe Val Val Ser Arg Thr
        115                 120                 125

Pro Thr Gln Val Ala Ser His Ala Gln Lys Tyr Phe Ile Arg Gln Ser
    130                 135                 140

Asn Met Thr Arg Arg Lys Arg Arg Ser Ser Leu Phe Asp Met Val Pro
145                 150                 155                 160

Asp Glu Ser Met Asp Leu Pro Pro Leu Pro Gly Gly Gln Glu Pro Glu
                165                 170                 175

Thr Gln Val Leu Asn Gln Pro Ala Leu Pro Pro Lys Glu Glu Glu
            180                 185                 190

Glu Val Asp Ser Met Glu Ser Asp Thr Ser Ala Val Ala Glu Ser Ser
        195                 200                 205

Ser Ala Ser Ala Ile Met Pro Asp Asn Leu Gln Ser Thr Tyr Pro Val
    210                 215                 220

Ile Val Pro Ala Tyr Phe Ser Pro Phe Leu Gln Phe Ser Val Pro Phe
225                 230                 235                 240

Trp Gln Asn Gln Lys Asp Glu Asp Gly Pro Val Gln Glu Thr His Glu
                245                 250                 255

Ile Val Lys Pro Val Pro Val His Ser Lys Ser Pro Ile Asn Val Asp
            260                 265                 270

Glu Leu Val Gly Met Ser Lys Leu Ser Ile Gly Glu Ser Asn Gln Glu
```

```
            275                 280                 285
Thr Glu Ser Thr Ser Leu Ser Leu Asn Leu Val Gly Gly Gln Asn Arg
    290                 295                 300

Gln Ser Ala Phe His Ala Asn Pro Pro Thr Arg Ala Gln Ala
305                 310                 315
```

<210> SEQ ID NO 10
<211> LENGTH: 42
<212> TYPE: DNA
<213> ORGANISM: Artificial Sequence
<220> FEATURE:
<223> OTHER INFORMATION: Synthetically generated oligonucleotide

<400> SEQUENCE: 10
aattctatcc atatccatat ccatatccat atccatatcc ac                42

<210> SEQ ID NO 11
<211> LENGTH: 38
<212> TYPE: DNA
<213> ORGANISM: Artificial Sequence
<220> FEATURE:
<223> OTHER INFORMATION: Synthetically generated oligonucleotide

<400> SEQUENCE: 11
gtggatatgg atatggatat ggatatggat atggatag                    38

<210> SEQ ID NO 12
<211> LENGTH: 29
<212> TYPE: DNA
<213> ORGANISM: Artificial Sequence
<220> FEATURE:
<223> OTHER INFORMATION: Primer

<400> SEQUENCE: 12
aaactcgaga atgacctccc aggcggcga                              29

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
atcgaattct cattggtgca tcttggccgg a                           31

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
aaactcgaga atgcccaacc tcacctcca                              29

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
agcgaattct tatataaaac tggtgaa                                27

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
aaactcgagt atgacgaggc ggtgctcgca                                    30

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
atcgaattct catgcctgtg cccttgt                                       27

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
ccagaattct gcaaagatgg ataaa                                         25

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
ccactcgagc tctcttttt tgggt                                          25

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
ccagaattca gatgaagcta ctgtct                                        26

<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21
ccactcgagt tcgatacagt caactgt                                       27

PLANT MYB PROTEINS

RELATED APPLICATION

This application claims priority to U.S. Provisional Application Ser. No. 60/399,999, filed on Jul. 31, 2002, the contents of which are incorporated by reference in their entirety.

BACKGROUND

MYB proteins are a group of transcription factors. The cellular myb proto-oncogene (c-myb) is involved in the proliferation and/or differentiation of haematopoietic cells (Graf (1992) Curr. Op. Gen. Devel. 2, 249-255). Common to all MYB gene products is a strongly conserved DNA-binding domain located at the N-terminal end. In animals, this DNA-binding domain consists of three imperfect repeats of approximately 51-52 amino acids each (designated R1, R2, and R3) with three highly conserved tryptophan residues regularly spaced by 18 or 19 amino acids (Weston (1999) Curr. Op. Gene Devel. 8, 76-81). In plants and yeast, the predominant MYB proteins have two repeats (R2 and R3) (Martin and Paz-Ares (1997) Trends Genet. 13, 67-73; Jin and Martin (1999) Plant Mol. Biol. 41, 577-585). However, MYB proteins containing only one repeat or three repeats have also been identified in plants (Baranowskij, et al. (1994) EMBO J 13, 5383-5392; Kirik and Bäumlein (1996) Gene 183, 109-113; Feldbrügge, et al. (1997) Plant J. 11, 1079-1093; Wang, et al. (1997) Plant Cell 9, 491-507; Braun and Grotewold (1999) Plant Physiol. 121, 21-24).

SUMMARY

The invention is based on the discovery of three novel rice genes encoding Myb proteins, designated OsMYBS1, OsMYBS2, and OsMYBS3, respectively. These proteins bind to promoters containing one or more copies of a TATCCA sequence and regulate the promoter activity.

The full-length OsMYBS1, OsMYBS2, and OsMYBS3 cDNAs (designated SEQ ID NOs:1-3, respectively), with the start and stop codons underlined, are shown below:

```
OsMYBS1 cDNA:
GTGCGAGATCCACCACCCGATGACCTCCCAGGCGGCGACGACGACGACCACGGCGGCGGCGGCGGCGGCGTGGACCA  (SEQ ID NO: 1)

GGGAGGACGACAAGGCGTTCGAGAACGCGCTCGCGGCTTGCGCGGCGCCGCCGCCCGCGGACGGAGGCGCGCCCGAC

GACGACTGGTTCGCCGCGCTCGCCGCGAGCGTGCCCGGGGCGAGGTCGGCGGAGGAGGTGCGGAGGCACTACGAGGC

GCTGGTGGAGGACGTCGCGGCCATCGACGCGGGCCGCGTCCCGCTCCCGCGCTACGCCGGGGAGGAGTCCGCGGCGC

CGCCCGACGGAGCCGGAGCCGCCGCCGCCGCGTCCAAGGACGGCGGACACCGGCCCGACGAGCGCAAGGGCGGCGGC

GGCGGGTACGACGGCGGCAAGAGCTGCTCCAAGGCGGAGCAGGAGAGGCGCAAGGGCATCCCATGGACGGAGGAAGA

GCACAGGCTGTTCTTGCTGGGGCTGGACAAGTTCGGCAAGGGGGACTGGCGGAGCATCTCGCGCAACTTCGTCATCT

CGCGGACGCCAACGCAGGTGGCGAGCCACGCGCAGAAGTACTTCATCCGCCTCAACTCCATGAACCGCGACCGCCGC

CGCTCCAGCATCCACGACATCACCAGCGTCACCGCCGGCGATCAGGTCGCCGCGCAGCAGGGCGCCCCGATCACCGG

CCACCAGGCCACGGGCAACCCCGCGGCGGCGGCGCTGGGCCCGCCGGGCATGAAGCACCACCACCACCACCACCCGG

GCGGCGCGCCGCCGCCCATGCCCATGTACAGCGCCGCGCCCATGGGCCACCCCGTCGCCGGCCACATGGTGCCCGCC

GCCGTCGGCACGCCGGTGGTGTTCCCGCCGGGCCACGCGCCGTACGTCGTGCCCGTCGGCTACCCGGCGCCTCCGGC

CAAGATGCACCAATGACGCGCCATGGACGGACATGAGCAGCATTTCTTCCTCCTCCTTTCTTGATGTCAATCTTGAT

TTGTTCTTTGTGTAGTCGCCGGCTCATCGTCCCTGATCATCTTGTTCTTCTCACAATCTCACTAATGTAAACATACA

TAGATCAGATGCCAAGAGTGCAGGGATTGGGGATTAAAGGCGAATAAGTAAAGTATTTTGCTGACTGTTTGCAAGTG

ATCATCACGTACACCCGGTGAAAGCTTAGCTCCAAATGTGGATGTAATTAGCAGCGGCCTTCCGTACGTGGTGGCGC

CGATCGATGATCTTGCAGGGGTTGCAATTAGGGATTGATTTCCATTTTGCTGATGTAAATTTGCCAACTGTCTCATT

GGACCAAAAAAAAAAAAAAAA

OsMYBS2 cDNA:
CGAGGTCCGCGGCGGCGGCGGAGTTGACGAGGAGGAGTACGAGGAGGAGGAGGTGGAGGGTGGATTGTTCATCA  (SEQ ID NO: 2)

AGAAGAGCTCCAGTATGCCCAACCTCACCTCCATCGACCCGCTGCCGGTGCCGGCCGACGGCGGCAAACGGCGCGCC

TCCGACGACTCCGAGCTCGCCTCCGGCCAGCAGAAGCGCCGCCGCCGCAAGGTGCAGGAGAGGAAGAAAGGGGTACC

ATGGACTGAGGAGGAGCACAAGAAATTCCTGGAAGGGCTGAGGCAGCTGGGGAAAGGGGACTGGAGAGGCATCTCCA

AGAACTTTGTGACCAGCAGGACGGCGACTCAGGTGGCCAGCCACGCCCAGAAGTACTTCCTCCGGCAGACCAACCCT

GGCAAAAAGAAGCGCCGGGCCAGCCTCTTTGATGTTGTTGCTGAGTGCAGTGATGATCAACTTCCAAGTCCTCAGAG

TGTTGGAACTAAGCCTCCTACCCAGGATATAATTCATACAGATCGCGGCGATGTCCCGATACTAAGCTATCCAGTTG

CTAGAGGCTTTAGAGGCGATAGCGTGCAGGTTGATGAACTAACTGAATATGTGAAGAGATTAAAGGCCGCCGAGGAC
```

-continued

```
ATGTCGCTCTCCATGATCTCTGGACTGGAAATGGCATCATCATCCATCAGCAGTCTAGAGCTCAGTATCGCGCCCTC

TCATTTGCGGATCGACGGGGCCATCAAGGGGCTGGGATCCAAACCCAATTTTCCCCCGAAGGAATTTGGATCGGCTT

CAGCTACTGTTTTTTGTCCCCCCTGTTGTTGTTTGTTGTTGTTGTTTTTTTTTTTTTTTTGCGGGGGTTGTTTGT

TGTTGTTGTTGTTGTAGTTGTCATGCTAACTTTGTATTTGGGTCATGTGGGGTTTCTTTCACCAGTTTTATATAATA

CAGAGAGAATGTCAGTCCCTTCCGAGACATGTTTAAAAAAAAAAAAAAAAAAAAAAAAAAAAAAAAAAAAAAAAAAA

AAAAAAAAAA
```

OsMYBS3 cDNA:
```
ATCGATCGATCGATCTCCATAGGTGGGGAAGGGAAGCTTTGGAAGGTGGAGGGACGGAGGGGGGGATGACGAGGCG    (SEQ ID NO: 3)

GTGCTCGCACTGCAGCCACAACGGGCACAACTCGCGGACGTGCCCCAACCGCGGGGTCAAGATCTTCGGGGTGCGCC

TCACCGATGGCTCCATCCGCAAGAGCGCCAGCATGGGGAACCTCTCCCTCCTCTCCTCCGCCGCCGGATCCACCAGC

GGCGGCGCCTCCCCCGCCGACGGCCCCGACGCCGCCCCCACCGCCGCCGACGGCTACGCCTCCGACGACTTCGTCCA

GGGCTTCTCCTCCGCCACCCGCGACCGCAAGAAGGGTGTTCCTTGGACTGAAGAAGAACACCGGAGGTTTTTGCTTG

GATTGCAAAAGCTTGGCAAAGGTGATTGGCGAGGAATCTCTCGTAATTTCGTGGTCTCAAGAACACCTACTCAAGTA

GCCAGTCATGCTCAGAAATATTTTATACGCCAATCCAATATGACCAGAAGGAAAAGAAGGTCTAGCCTTTTTGACAT

CACTACCTCCACCGAAGGAGGAAGAGGAGGTAGATTCTATGGAGTCAGATACTTCTGCCGTTGCAGAGAGCTCTTCC

GCTTCTGCTATCATGCCAGATAATTTGCAGTCGACCTATCCAGTGATTGTTCCAGCTTATTTCTCGCCCTTTTTGCA

ATTCTCGGTTCCTTTCTGGCAAAATCAGAAAGATGAAGATGGTCCTGTGCAAGAAACACATGAGATTGTCAAGCCTG

TTCCAGTTCATTCAAAGAGCCCAATCAACGTTGATGAGCTTGTTGGCATGTCGAAGCTCAGCATAGGAGAGTCCAAT

CAAGAGACAGAGTCTACTTCTCTTTCATTAAATCTGGTAGGAGGTCAAAATAGACAATCAGCTTTCCATGCAAATCC

ACCAACAAGGGCACAGGCATGATCTGGTTGTGCACACAACTGCATTTAGATGAATCCCAGGCAAAATAAGCTTTGCC

TCCTTGTTTTTTTGTTTTTATTTTAAGATTAACCGTTCTCCGTAGTCTGTATCATGTGCTGTAAGTTATGCTATGTA

TGAATGTATCTGTTGTTTGTCTGGCACACATGATAAATCACTCTATGTTAACAAAATCAGTAATGGTAGTGCTGATC

TTCGTGGTTGTACTGTTGTAAACTCTTTTATAAGAAAAAAAAATATTAGTTAGTC
```

The nucleic acid sequences encoding the OsMYBS1, OsMYBS2, and OsMYBS3 proteins (i.e., from the ATG start codon to the codon immediately before the stop codon in SEQ ID NOs:1-3) are designated SEQ ID NOs:4-6, respectively. The OsMYBS1, OsMYBS2, and OsMYBS3 proteins (designated SEQ ID NOs:7-9) encoded by the above cDNAs are shown below:

OsMYBS1 protein:
```
MTSQAATTTTTAAAAAAWTREDDKAFENALAACAAPPPADGGAPDDDWFAALAASVPGARSAEEVRRHYEALVEDVA    (SEQ ID NO: 7)

ATDAGRVPLPRYAGEESAAPPDGAGAAAAASKDGGHRRDERKGGGGGYDGGKSCSKAEQERRKGIPWTEEEHRLFLL

GLDKFGKGDWRSISRNFVISRTPTQVASHAQKYFIRLNSMNRDRRRSSTHDITSVTAGDQVAAQQGAPITGHQATGN

PAAAALGPPGMKHHHHHHPGGAPPPMPMYSAAPMGHPVAGHMVPAAVGTPVVFPPGHAPYVVPVGYPAPPAKMHQ
```

OsMYBS2 protein:
```
MPNLTSIDPLPVPADGGKRRASDDSELASGQQKRRRRKVQERKKGVPWTEEEHKKFLEGLRQLGKGDWRGISKNFVT    (SEQ ID NO: 8)

SRTATQVASHAQKYFLRQTNPGKKKRRASLFDVVAECSDDQLPSPQSVGTKPPTQDIIHTDRGDVPTLSYPVARGFR

GDSVQVDELTEYVKRLKAAEDMSLSMISGLEMASSSISSLELSIAPSHLRTDGAIKGLGSKPNFPPKEFGSASATVF

CPPCCCLLLLFFFFFFAGVVCCCCCCSCHANFVFGSCGVSFTSFT
```

OsMYBS3 protein:
```
MTRRCSHCSHNGHNSRTCPNRGVKIFGVRLTDGSIRKSASMGNLSLLSSAAGSTSGGASPADGPDAAPTAADGYASD    (SEQ ID NO: 9)
```

```
-continued
DFVQGFSSATRDRKKGVPWTEEEHRRFLLGLQKLGKGDWRGISRNFVVSRTPTQVASHAQKYFIRQSNMTRRKRRSS

LFDMVPDESMDLPPLPGGQEPETQVLNQPALPPPKEEEEVDSMESDTSAVAESSSASAIMPDNLQSTYPVTVPAYFS

PFLQFSVPFWQNQKDEDGPVQETHEIVKPVPVHSKSPINVDELVGMSKLSTGESNQETESTSLSLNLVGGQNRQSAF

HANPPTRAQA
```

Accordingly, the invention features a pure polypeptide including an amino acid sequence at least 70% (e.g., at least 75, 80, 85, 90, or 95; or 100%) identical to SEQ ID NO:7, 8, or 9. When expressed in a cell, the polypeptide binds to a promoter and regulates transcription from the promoter. The cell can be a plant cell, in particular, a monocot plant cell (e.g., a cereal plant cell such as a rice cell or a barley cell). The promoter can contain one or more copies of a TATCCA sequence or its variant. Moreover, an HvMYBGa protein can be co-expressed in the cell. HvMYBGa interacts with the OsMYBS proteins and they together cooperatively regulate the expression of a gene. The polypeptides of the invention can be used for producing OsMYBS antibodies (either monoclonal or polyclonal). These antibodies in turn are useful for detecting the presence and distribution of OsMYBS proteins in tissues and in cellular compartments. For example, such antibodies can be used to verify the expression of OsMYBS proteins in a transgenic plant.

A "pure polypeptide" refers to a polypeptide substantially free from naturally associated molecules, i.e., it is at least 75% (e.g., at least 80, 85, 90, or 95; or 100%) pure by dry weight. Purity can be measured by any appropriate standard method, for example, by column chromatography, polyacrylamide gel electrophoresis, or HPLC analysis.

The "percent identity" of two amino acid sequences is determined using the algorithm of Karlin and Altschul ((1990) Proc. Nati. Acad. Sci. USA 87, 2264-2268), modified as in Karlin and Altschul ((1993) Proc. Natl. Acad. Sci. USA 90, 5873-5877). Such an algorithm is incorporated into the XBLAST programs of Altschul, et al. ((1990) J. Mol. Biol. 215, 403-410), available on the world wide web. BLAST protein searches are performed with the XBLAST program, score=50, wordlength=3. Where gaps exist between two sequences, Gapped BLAST is utilized as described in Altschul, et al. ((1997) Nucleic Acids Res. 25, 3389-3402). When utilizing BLAST and Gapped BLAST programs, the default parameters of the respective programs (e.g., XBLAST) are used.

The invention further features an isolated nucleic acid (e.g., a vector) encoding a polypeptide of the invention, and a cell (in a culture or in a transgenic plant) containing a nucleic acid of the invention. The cell can be a plant cell, in particular, a monocot plant cell (e.g., a cereal plant cell such as a rice cell or a barley cell). An example of a nucleic acid within the invention includes an isolated nucleic acid characterized in that it hybridizes under stringent conditions to SEQ ID NO: 1, 2, or 3, or a complementary sequence thereof. Such a nucleic acid can be at least 15 (e.g., at least 30, 50, 100, 200, 500, or 1000) nucleotides in length. These nucleic acids and cells can be used for generating a transgenic plant or producing the polypeptides of the invention. For instance, the nucleic acids of the invention can be used to determine whether an OsMYBS mRNA is expressed in a tissue or cell. The nucleic acids can be used as primers in PCR-based detection methods, or as labeled probes in nucleic acid blots (e.g., Northern blots).

An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

By hybridization under "stringent conditions" is meant hybridization at 65° C., 0.5×SSC, followed by washing at 45° C., 0.1×SSC.

A plant cell of the invention can be cultivated to generate a transgenic plant. The transgenic plant can be a monocot plant, e.g., a cereal plant such as rice or barley. The genome of such a transgenic plant contains a transgene that includes a nucleic acid characterized in that it hybridizes under stringent conditions to SEQ ID NO:1, 2, or 3, or a complementary sequence thereof. The transgene, when expressed in a cell, regulates the activity of promoters, e.g., those containing one or more copies of a TATCCA sequence or its variant.

In addition, the invention features a method of expressing a transcript in a cell (e.g., a plant cell). The method involves introducing into a cell a vector that contains a nucleic acid encoding a transcript and expressing the transcript in the cell. The transcript is characterized in that it hybridizes under stringent conditions to SEQ ID NO:1, 2, or 3, or a complementary sequence thereof. The transcript can encode a polypeptide of the invention, which regulates the activity of promoters, e.g., those containing one or more copies of a TATCCA sequence or its variant. On the other hand, the transcript can be an anti-sense RNA, which inhibits the expression of endogenous OsMYBS genes, thereby deregulates the activity of promoters, e.g., those containing one or more copies of a TATCCA sequence or its variant.

The invention also features a method of identifying a compound that modulates the activity of the polypeptide of this invention, i.e., the ability of the polypeptide to regulate expression of a gene. The method includes (1) introducing a test compound into a system containing a nucleic acid having a promoter containing one or more copies of an element that binds to the polypeptide, e.g., a TATCCA sequence, the promoter being operably linked to a reporter gene; and (2) determining an expression level of the reporter gene in the system. The expression level of the reporter gene in the presence of the test compound, if different from that in the absence of the test compound, indicates that the test compound is a candidate for modulating the activity of the polypeptide. The system, which can be a cell or a cell-free system (e.g., a cell lysate) may or may not contain the polypeptide of this invention. In the latter case, to practice the method, one can introduce into the system the polypeptide or a nucleic acid encoding the polypeptide. The test compound can be a small molecule, a polypeptide, or a nucleic acid that encodes a test polypeptide or binds to the polypeptide of this invention. The reporter gene can be a LacZ gene, a green fluorescent protein gene, a GUS gene, or a luciferase gene.

This invention provides a system for highly regulated expression of endogenous or exogenous genes in a plant cell or a transgenic plant. The details of some embodiments of the invention are set forth in the accompanying description below. Other features, objects, and advantages of the invention will be apparent from the detailed description, and from the claims.

DETAILED DESCRIPTION

Expression of α-amylase genes in cereals is induced by both gibberellin (GA) and sugar starvation. All α-amylase genes isolated from cereals contain a TATCCA element or its variant at positions approximately 90 to 150 bp upstream of the transcription start site. The TATCCA element is an important component of the GA response complex (GARC) and the sugar response complex (SRC) of α-amylase gene promoters.

Three cDNA clones encoding novel MYB proteins with single DNA binding domain have been isolated from a rice suspension cell cDNA library and designated OsMYBS1, OsMYBS2 and OsMYBS3. Unexpectedly, OsMYBS proteins bind specifically to the TATCCA element in vitro. In vivo, OsMYBS1 and OsMYBS2 bind to the TATCCA element and transactivate a promoter containing the TATCCA element when sugar is provided, whereas OsMYBS3 represses transcription of the same promoter under sugar starvation. Furthermore, these three OsMYBS proteins cooperate with a GA-regulated transcription factor, GAMyb (HvMYBGa), in transactivation of a low pI barley α-amylase gene promoter in the absence of GA.

In one aspect, the present invention features pure OsMYBS polypeptides (e.g., SEQ ID NOs:7-9), including functional OsMYBS polypeptides. A "functional polypeptide" refers to a polypeptide which possesses biological activity equivalent to that of a wild-type OsMYB protein, e.g., a fragment of a wild-type OsMYBS protein.

In another aspect, the invention features isolated OsMYBS nucleic acids (i.e., DNA, cDNA, and RNA) characterized in that they hybridizes under stringent conditions to SEQ ID NO:1, 2, or 3, or a complementary sequence thereof. The nucleic acids of the invention include sequences that are degenerate as a result of the genetic code.

A nucleic acid of the invention can be expressed in vitro by DNA transfer into a suitable host cell by methods known in the art. For example, the nucleic acid can be inserted into a recombinant expression vector. A variety of host-expression vector systems can be utilized to express a nucleic acid of the invention. These include, but are not limited to, microorganisms such as bacteria transformed with recombinant bacteriophage DNA, plasmid DNA, or cosmid DNA expression vectors; yeast transformed with recombinant yeast expression vectors; plant cell systems infected with recombinant virus expression vectors (e.g., cauliflower mosaic virus, CaMV; tobacco mosaic virus, TMV), or transformed with recombinant plasmid expression vectors (e.g., Ti plasmid). Isolation and purification of recombinant polypeptide, or fragments thereof, provided by the invention, can be carried out by conventional means including preparative chromatography and immunological separations involving monoclonal or polyclonal antibodies.

The invention also features antibodies against an OsMYBS polypeptide, including monoclonal antibodies and polyclonal antibodies. The term "antibody" includes intact molecules as well as fragments thereof, such as Fab, F(ab')$_2$, and Fv which are capable of binding to an epitopic determinant present in an OsMYBS polypeptide. Methods of making monoclonal and polyclonal antibodies and fragments thereof are known in the art. See, for example, Harlow and Lane (1988) Antibodies: A Laboratory Manual, Cold Spring Harbor Laboratory, New York.

Also within the scope of the invention is a transgenic plant, the genome of which contains a transgene that includes a nucleic acid characterized in that it hybridizes under stringent conditions to SEQ ID NO:1, 2, or 3, or a complementary sequence thereof. The transgene, when expressed in a cell, regulates the activity of promoters, e.g., those containing one or more copies of a TATCCA sequence or its variant.

As used herein, the term "plant" refers to either a whole plant, a plant part, a plant cell, or a group of plant cells, such as plant tissue. Plantlets are also included within the meaning of "plant". Plants included in the invention are any plants amenable to transformation techniques, including angiosperms, gymnosperms, monocotyledons, and dicotyledons. Examples of monocotyledonous plants include, but are not limited to, asparagus, field and sweet corn, barley, wheat, rice, sorghum, onion, pearl millet, rye, and oats. Examples of dicotyledonous plants include, but are not limited to, tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers, and various ornamentals. Woody species include poplar, pine, sequoia, cedar, oak, etc.

Transgenic plants can be produced using methods well known in the art. See, for example, Weissbach and Weissbach (1988) Methods for Plant Molecular Biology, Academic Press, NY, Section VIII, pp. 421-463; Grierson and Corey (1988) Plant Molecular Biology, 2d Ed., Blackie, London, Ch. 7-9; and Horsch, et al. (1985) Science 227, 1229.

In addition, the invention features a method of expressing a transcript in a cell (e.g., a plant cell). The method involves introducing into a cell a vector that contains a nucleic acid encoding a transcript and expressing the transcript in the cell. The transcript is characterized in that it hybridizes under stringent conditions to SEQ ID NO:1, 2, or 3, or a complementary sequence thereof. The transcript can be an RNA that interferes with the function of another RNA in a plant cell, for example, preventing an mRNA from being translated into a polypeptide, or triggering specific RNA degradation to facilitate targeted post-transcriptional gene silencing (Mol et al. (1990) FEBS Lett 268(2), 427-30; and Fire et al. (1998) Nature 391, 806-811). Alternatively, the transcript can encode a polypeptide for over-production of the polypeptide in transformed plant cells or a transgenic plant. Alterations in OsMYBS expression result in changes in expression of genes regulated by OsMYBS proteins, e.g., those directed by promoters containing one or more copies of a TATCCA sequence or its variant.

Also within the scope of this invention is a method of identifying a compound that modulates the ability of the above-described polypeptide (e.g., OsMYBS) to regulate expression of a gene. The compound can be used to enhance or repress the expression of a gene regulated by the polypeptide, e.g., α-amylase gene. To identify the compound, one can introduce a test compound into a system containing a nucleic acid having a promoter containing one or more copies of an element that binds to the polypeptide, e.g., a TATCCA sequence. The promoter is operably linked to a reporter gene, such as a LacZ gene, a green fluorescent protein gene, a GUS gene, or a luciferase gene. One can then determine an expression level, e.g., the mRNA or protein level, of the reporter gene in the system by standard methods. The expression level of the reporter gene in the presence of the test compound, if statistically different from that in the absence of the test compound, indicates that the test compound is a candidate for modulating the activity of the polypeptide. The system can be a cell containing endogenous OsMYB, e.g., a rice or barley cell, or a cell lacking OsMYB, e.g., a yeast cell. In the latter case, to practice the method, one can express OsMYB in the cell by introducing into it an expression vector encoding the polypeptide. The system can also be a cell-free system well known in the art, such as a cell lysate system.

The test compound can be a small molecule compound, a polypeptide, or a nucleic acid that encodes a test polypeptide or binds to the polypeptide of this invention. The test compound can be obtained from compound libraries, such as peptide or peptoid libraries. The libraries can be spatially addressable parallel solid phase or solution phase libraries. See, e.g., Zuckermann et al. J Med Chem 37, 2678-2685, 1994; and Lam Anticancer Drug Des 12:145, 1997. Methods for the synthesis of compound libraries are well known in the art, e.g., DeWitt et al. PNAS USA 90:6909, 1993; Erb et al. PNAS USA91:11422, 1994; Zuckermann et al. J Med Chem 37:2678, 1994; Cho et al. Science 261:1303, 1993; Carrell et al. Angew Chem Int Ed Engl 33:2059, 1994; Carell et al. Angew Chem Int Ed Engl 33:2061, 1994; and Gallop et al. J Med Chem 37:1233, 1994.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Materials and Methods

1. Rice Cell Culture

A suspension cell culture of rice (*Oryza sativa* cv. *Tainan* 5) was established as previously described (Yu, et al. (1991) J. Biol. Chem. 266, 21131-21137). Cells were subcultured every 7 days by transferring approximately 0.5 ml of cells into 25 ml of fresh liquid Murashige and Skoog medium (Murashige and Skoog (1962) Physiol. Plant 15, 473-497) containing 3% sucrose in a 125-ml flask. Cells were cultured on a reciprocal shaker at 120 rpm and incubated at 26EC in the dark.

2. Plasmids

Plasmid αAmy8-C carries a 1.4-kb rice α-amylase cDNA insert in pBluescript KS+(Stratagene) (Yu, et al. (1992) Gene 122, 247-253). Plasmid pcRAc1.3 contains a 1.4-kb rice actin gene (Act1) cDNA insert in pBluescript II-KS (McElroy, et al. (1990) Plant Mol. Biol. 15, 257-268). Plasmid pRY18 carries a 3.8 kb DNA fragment that contains a rice genomic rDNA cluster, including the 3' half portion of 18S rRNA gene, the complete 5.8S rRNA gene, and the 5' half portion of the 25S rRNA gene in pUC13 (Sano and Sano (1990) Genome 33, 209-218). Plasmid pGAMyb contains the HvMYBGa cDNA fused between the maize ubiquitin (Ubi) promoter and the nopaline synthase (Nos) terminator (Cercós, et al. (1999) Plant J. 19, 107-118). Plasmid pAHC18 contains the luciferase (Luc) cDNA fused between the Ubi promoter and the Nos terminator (Bruce, et al. (1989) Proc. Natl. Acad. Sci. USA 86, 9692-9696). Plasmid pAmy32b-GUS contains the 331-bp promoter region, the entire 5' untranslated sequence, and the first intron of Amy32b fused to the GUS coding sequence and the 3'untranslated region of Amy32b (Gómez-Cadenas, et al. (1999) Proc. Natl. Acad. Sci. USA 96, 1767-1772). A reporter construct, p3Luc.18, contains a sugar response sequence (SRS, −186 to −82 nucleotide) of rice α amylase, αAmy3. The SRS contains three motifs: a GC box, a G box, and the TATCCA element, essential for high level sugar starvation-induced promoter activity in rice protoplasts (Lu et al. (1998) J. Biol. Chem. 273, 10120-10131). The SRS is fused upstream to the CaMV35S minimal promoter-Luc chimeric gene. Another reporter construct, T7, contains a modified αAmy8SRS/GARS promoter. This promoter has a GC box, a G box, a gibberellin response element (GARE), two copies of the TATCCA element, all of which are linked upstream to the CaMV35S minimal promoter-Luc chimeric gene.

3. South-western Screening of cDNA Library

Rice suspension cells were cultured in sucrose-containing medium for 5 days and transferred to sucrose-containing (+S) or sucrose-free (−S) medium for 4 h. Cells were collected and total RNA was purified. Poly(A)$^+$ RNA was further purified using an oligo(dT) cellulose spin column (5 Prime→3 Prime). The poly(A)$^+$ RNA isolated from −S cells was used to construct a cDNA library in Lambda GEM-2 vector (Promega). *E. coli* strain Y1090 (Stratagene) served as the bacterial host. For screening and plaque purification, the 416-bp DNA fragment containing eight tandem repeats of the −133 to −82 region of the αAmy3 promoter was excised with PstI and XhoI from p3Luc.44 (Lu, et al. (1998) J. Biol. Chem. 273, 10120-10131) annd used as a probe for the cDNA library screening. The library was screened according to the method of Singh, et al. (1988) Cell 52, 415-423. Positive phage plaques were isolated and phage DNA was purified for further characterization.

4. Plasmid Construction

OsMYBS1 and OsMYBS2 cDNAs were excised from Lambda GEM-2 with SalI and NotI, and inserted into the same sites in pBluescript (Stratagene) to generate pBS-S1 and pBS-S2, respectively. There is one SalI site within the OsMYBS3 cDNA, therefore, OsMYBS3 cDNA was excised from Lambda GEM-2 with EcoRI and NotI and inserted into the same sites in pBluescript to generate pBS-S3. pAHC18 was digested with BamHI to remove the Luc cDNA insert and was then end-blunted. OsMYBS1 and OsMYBS2 were excised from pBS-S1 and pBS-S2, respectively, with SalI and NotI and end-blunted. OsMYBS3 was excised from pBS-S3 with EcoRI and NotI and end-blunted. The OsMYBS cDNAs were then individually ligated with the truncated pAHC18 to generate an Ubi-OsMYBS-Nos fusion gene. An expression vector encoding Ubi-OsBZ8, pUBZ8, was also constructed. OsBZ8 (GenBank Access No.: U42208) is a basic leucine zipper (bZIP) DNA binding protein. To make this vector, pAHC18 was digested with BamHI to remove the Luc cDNA insert and blunt-ended. The OsBZ8 cDNA was excised from a pBluescript plasmid with PstI and SpeI, blunt-ended, and ligated to the pAHC18.

5. Genomic DNA Gel Blot Analysis

Genomic DNA was isolated from rice calli according to the method of Sheu, et al. (1996) J. Biol. Chem. 271, 26998-27004. Ten mg of genomic DNA was digested with restriction enzymes, fractionated in a 0.8% agarose gel, and transferred to a nylon membrane (MSI). Hybridization was performed at 42° C. using $^{32}P$ random primer-labeled OsMYBS gene-specific DNA as a probe. pBS-S1 was digested with SacII, and the 613-bp DNA fragment containing the 220-bp coding region and the 393-bp 3'untranslated region of OsMYBS1 cDNA served as OsMYBS1-specific DNA. pBS-S2 was digested with Sacd, and the 334-bp DNA fragment containing the 241-bp coding region and the 93-bp 3'untranslated region of OsMYBS2 cDNA served as OsMYBS2-specific DNA. pBS-S3 was digested with SacI, and the 599-bp DNA fragment containing the 332-bp coding region and the 267-bp 3'untranslated region of OsMYBS3 served as OsMYBS3-specific DNA.

6. RNA Gel Blot Analysis

Total RNA was purified from rice suspension cells using TRIZOL reagent (GIBCO-BRL). $\alpha$-$^{32}P$-labeled DNA probes were prepared, and RNA gel blot analysis was performed as described (Sheu, et al. (1996) J. Biol. Chem. 271, 26998-27004). In cases when the membrane blot was sequentially hybridized with various probes, the membrane was stripped and rehybridized as described (Sheu, et al., (1994) Plant J. 5, 655-664). Plasmid DNAs of αAmy8-C and pcRAc1.3 were digested with EcoRI. αAmy3 and αAmy8 gene-specific DNAs were prepared as described (Sheu, et al., (1996) J. Biol. Chem. 271, 26998-27004). These insert DNAs were individually isolated, labeled with $\alpha$-$^{32}P$, and used as probes. A DNA fragment containing 25S, 18S and 5.8S rDNAs was excised from pRY18 using BamHI, labeled with $\alpha$-$^{32}P$, and used as a probe to equalize RNA loading.

7. Expression and Purification of Recombinant Proteins

OsMYBS was digested with SalI and NotI and ligated into the same sites in pET28b(+) (Novagen) to generate pET-S1, pET-S2, and pET-S3. The three plasmids were each transferred into *E. coli* strain BL21(DE3), and OsMYBS1, OsMYBS2, and OsMYBS3 were expressed. Purification of the OsMYBS proteins was performed according to the instructions provided by Novagen. The protein concentration was determined with Bradford reagent (Bio-Rad).

8. Gel Mobility Shift Assay

The gel mobility shift assay was performed essentially as previously described (Lu, et al. (1998) J. Biol. Chem. 273, 10120-10131), except that the DNA-protein binding reaction was carried out by incubation of 0.02 ng of $^{32}P$-labeled oligonucleotide with 0.2 µg recombinant OsMYBS purified from *E. coli* and 1 µg poly(dI-dC) in a total volume of 20 µl solution. A DNA fragment containing the TATA box was prepared as previously described (Lu, et al. (1998) J. Biol. Chem. 273, 10120-10131).

9. Construction of the Yeast Reporter Strains

The DNA fragment containing eight tandem repeats of −133 to −82 of the αAmy3 promoter was excised from p3Luc.44 (Lu, et al. (1998) J. Biol. Chem. 273, 10120-10131) with EcoRI and XhoI, end-blunted and inserted into the SmaI site in pLacZi (Clontech) to generate a 8x(TATCCA+F)-Cyc1 minimal promoter-LacZ fusion gene. The two complementary oligonucleotides 5'-AATTCTATC-CATATCCATATCCATATCCATATCCATATCCAC-3' (SEQ ID NO:10) and 5'-GTGGATATGGATATGGATATG-GATATGGATATGGATAG-3' (SEQ ID NO:11) were annealed and inserted into the EcoRI and SmaI sites of pLacZi to generate a 6xTATCCA-Cyc1 minimal promoter-LacZ fusion gene. These plasmids were linearized with NcoI and introduced into the genome of yeast strain YM4271, according to the MATCHMAKER One-Hybrid System protocol (Clontech), to generate the yeast reporter strains.

10. Yeast One-hybrid System for OsMYBS Binding Activity Assay

For construction of the GAD-OsMYBS fusion gene, the full length OsMYBS cDNAs were PCR-amplified using pBS-S1, pBS-S2 and pBS-S3 as the DNA templates and oligonucleotides OsMYBS1-5' (5'-AAA CTCGAGAATGACCTCCCAGGCGGCGA-3' (SEQ ID NO:12), XhoI site underlined) and OsMYBS1-3' (5'-ATC GAATTCTCATTGGTGCATCTTGGCCGGA-3' (SEQ ID NO:13), EcoRI site underlined) as primers for OsMYBS1, OsMYBS2-5' (5'-AAA CTCGAGAATGCCCAACCTCACCTCCA-3' (SEQ ID NO:14)), XhoI site underlined) and OsMYBS2-3' (5'-AGC GAATTCTTATATAAAACTGGTGAA-3' (SEQ ID NO:15)), EcoRI site underlined) as primers for OsMYBS2, and OsMYBS3-5' (5'-AAA CTCGAGTATGACGAGGCGGTGCTCGCA-3' (SEQ ID NO:16)), XhoI site underlined) and OsMYBS3-3' (5'-ATC GAATTCTCATGCCTGTGCCCTTGT-3' (SEQ ID NO:17)), EcoRI site underlined) as primers for OsMYBS3. The GAD sequence was PCR-amplified using pGAD-424 (Clontech) as the DNA templates and oligonucleotides GAD-5' (5'-CCAGAATTCTGCAAAGATGGATAAA-3' (SEQ ID NO:18)), EcoRI site underlined) and GAD-3' (5'-CCACTCGAGCTCTCTTTTTTTGGGT-3' (SEQ ID NO:19)), XhoI site underlined) as the primers. All the PCR products were digested with XhoI and EcoRI. The OsMYBS cDNAs were individually ligated with the GAD sequence in the XhoI site and inserted into the EcoRI site of pBluescript to generate pGAD-OsMYBS. pGAD-424 was digested with MluI and EcoRI to remove the 3' portion of the GAD domain. The GAD 3' portion-OsMYBS fusion genes were excised from pGAD-OsMYBS with MuII and EcoRI and inserted into the MluI and EcoRI sites of pGAD-424 to generate pGAD-OsMYBS-424 that contains the ADH1 promoter-GAD-OsMYBS fusion gene. These plasmids were individually introduced into the yeast reporter strain, which hosts the 8x(TATCCA+F)-Cyc1 minimal promoter-LacZ fusion gene or the 6xTATCCA-Cyc1 minimal promoter-LacZ fusion gene, according to the MATCHMAKER One-Hybrid System protocol (Clontech). β-Galactosidase activity in yeast was assayed.

11. Yeast One-hybrid System for OsMYBS Transactivation Assay

For construction of the GBD-OsMYBS fusion gene, the GBD sequence was PCR-amplified using pGBT9 (Clontech) as the DNA template and oligonucleotides GBD-5' (5'-CCA GAATTCAGATGAAGCTACTGTCT-3' (SEQ ID NO:20)), EcoRI site underlined) and GBD-3' (5'-CCA CTCGAGTTCGATACAGTCAACTGT-3' (SEQ ID NO:21)), XhoI site underlined) as primers. Because there is one XhoI cutting site within the GBD sequence, the PCR product was digested with EcoRI first and then partially digested with XhoI. The resulting DNA fragment was ligated with OsMYBS cDNA and inserted into the EcoRI site of pBluescript to generate pGBD-OsMYBS. pGAD-424 was digested with HindIII to remove the GAD sequence and end-blunted. The GBD-OsMYBS fusion genes were excised from pGBD-OsMYBS with EcoRI and HindIII, end-blunted, and ligated with the truncated pGAD-424 to generate pGBD-OsMYBS-424 that contains the ADH1 promoter-GBD-OsMYBS fusion gene. These plasmids were introduced into the yeast strain CG-1945 that hosts the 3xUAS-Cyc1 minimal promoter-LacZ and GAL1 promoter-HIS3 reporter constructs (Clontech). 3xUAS is three tandem repeats of a synthetic $UAS_G$17-mer consensus sequence that can be recognized by GBD. β-Galactosidase activity in yeast or growth of yeast cells on selective medium was assayed.

12. β-Galactosidase Activity and Yeast Cell Growth Assays

β-galactosidase activity in transformed yeast cells was quantified by using ONPG (o-nitrophenyl β-galactopyranoside) as the substrate. Transformed cells were selected in a medium containing 5 mM 3-aminotriazole but no histidine according to the Yeast Protocols Handbook (Clontech).

13. Barley Aleurone Tissue Transient Expression Assay

Particle bombardment of the barley (*Hordeum vulgare*) aleurone tissue and transient assay of GUS were performed essentially as described by Lanahan, et al. (1992) Plant Cell 4, 203-211 and Cercós, et al. (1999) Plant J. 19, 107-118. Bombarded barley embryoless half-seeds were incubated in a buffer (20 mM each of $CaCl_2$ and sodium succinate, pH 5.0) containing or lacking glucose or $GA_3$ for 20 h, and luciferase or GUS activity determined. All the bombardments were repeated at least four times.

14. Rice Embryo Transient Expression Assay

Rice seeds (*Oryza sativa* cv. *Tainung* 67) were placed in Petri dishes containing two pieces of sterile Whatman No.1 filter paper and a liquid MS salt mixture containing 2 mg/L 2,4-D (Toyofuku et al. (1998) FEBS Lett 428: 275-280). After incubation for 8 days, embryos with calli growth on their scutella were dissected from the endosperm. These embryos were then placed, with the scutellar side up, in plates containing solid MS medium. Each plate contained 24 embryos. Particle bombardment of the callus-containing embryos was performed as described in Umemura et al. (1998) Planta 204: 420-428. The embryos were co-bombarded with reporter, effector and internal control plasmids at a ratio of 1:1:0.25. pGL AC was used as the internal control. It contains the rice Act1 promoter fused upstream of the GUS cDNA (McElroy et al. (1990), Plant Mol Biol 15: 257-268). An unrelated yeast plasmid pRS426 was used in the co-bombardment as a negative control effector.

After bombardment, half of the embryos were incubated in MS medium containing 100 mM glucose or 100 mM mannitol for 18 hours. Total proteins were extracted from the embryos with a CCLR buffer [100 mM KH2 (PO4), pH7.8, 1 mM EDTA, 10% glycerol, 1% Triton X-100, 7 mM β-mercaptoethanol]. The GUS and luciferase activity assays were performed using standard methods. Each experiment was repeated three or four times.

Results

1. Three OsMYBS Genes Encode MYB Proteins with One DNA-binding Repeat

To obtain cDNAs encoding proteins that bind specifically to the TATCCA element, the South-western method was used to screen a cDNA library constructed from poly(A)+ mRNA prepared from 4-h sucrose-starved rice suspension cells. A 416-bp probe consisting of 8 tandem repeats of the −133 to −82 DNA fragment of αAmy3 promoter (Lu, et al. (1998) J. Biol. Chem. 273, 10120-10131), which contains the TATCCA element, was used. cDNA clones that interacted specifically with the probe were isolated and their sequences were analyzed. Three different genes were identified and designated OsMYBS1, OsMYBS2, and OsMYBS3. The open reading frames of OsMYBS1, OsMYBS2, and OsMYBS3 encode polypeptides of 306, 276, and 318 amino acid residues, respectively. The three OsMYBS proteins contain a highly conserved single DNA-binding domain that is also highly similar to the DNA-binding domains of other mammalian, Drosophila and plant MYB proteins.

Compared with other MYB proteins that contain a 1R in their DNA-binding domains, the 1R residues of the three OSMYBS proteins are most closely related to MybSt1 (StMYB1), and less related to AtMYBL2, PcMYB1, and CCA1 (AtMYBCCA1). StMYB1 transactivates the cauliflower mosaic virus 35S RNA gene (CaMV35S) promoter and is expressed in various organs of potato (Baranowskij, et al. (1994) EMBO J 13, 5383-5392). AtMYBL2 is expressed in Arabidopsis leaf but its function has not been characterized (Kirik and Bäumlein, (1996) Gene 183, 109-113). PcMYB1 interacts in vivo with a light-regulatory promoter unit and is expressed in *Petroselinum crispum* cell cultures and seedlings (Feldbrügge, et al. (1997) Plant J. 11, 1079-1093). AtMYBCCA1 binds to the promoter of an Arabidopsis light-harvesting chlorophyll a/b binding protein gene, Lhcb, and mediates phytochrome regulation of Lhcb (Wang, et al. (1997) Plant Cell 9, 491-507). The 1R sequence of OsMybS3 is most homologous to StMYB1 (92% identity) and somewhat homologous to OsMYBS1 (87% identity) and OsMYBS2 (85% identity), and the 1R sequences of OsMYBS1 and OsMYBS2 are least homologous (77% identity) to each other. There is very low homology among the N- and C-terminal regions outside the 1R regions of all the MYB proteins with 1R DNA-binding domains, except that OsMYBS3 and StMYB1 have 71% identity at the N-terminal 90-amino-acid region and 62% identity at the C-terminal 70-amino-acid region.

Comparison of amino acid residues between the 1R regions of the three OsMYBS proteins and the R2 and R3 repeats of the animal and plant MYB proteins shows that the 1R regions contain conserved tryptophan (W), glutamic acid (E), glycine (G), and arginine (R) at the same positions. The tryptophan residue, which plays a critical role in stabilizing the DNA binding domain of animal MYB proteins (Ogata, et al. (1992) Proc. Natl. Acad. Sci. USA 89, 6428-6432), is conserved at the first and second positions, but not at the third position, among most of the 1R regions. The putative base-contacting residues in the third helix of the animal MYB proteins are conserved in the plant R2R3 MYB proteins but not in the plant 1R MYB proteins.

The 3'untranslated regions of the three OsMYBS genes share very low homology (33-35% identity) and were used as gene-specific DNA probes for rice genomic DNA gel blot analysis. Only one band hybridized with each of the three gene-specific DNA probes. This result indicates that there is only one copy of each of the three OsMYBS genes in the rice MYB gene family.

2. OsMYBS Genes are Expressed in Various Rice Tissues and Barley Aleurones

The expression patterns of OsMYBS in rice were analyzed. Total RNA was purified from various rice tissues and subjected to gel blot analysis using OsMYBS-specific DNA as probes. OsMYBS1 is expressed in tissues above ground with the highest level in leaves. OsMYBS2 is expressed mainly in roots, leaves and senescence leaves at similar levels, and OsMYBS3 is expressed in all tissues with the highest level in senescence leaves.

To determine whether OsMYBS gene expression is regulated by sugars, total RNA was isolated from rice suspension cells cultured in the presence or absence of sucrose for 48 h and subjected to gel blot analysis using OsMYBS-specific DNAs as probes. The levels of OsMYBS1 and OsMYBS3 mRNAs are low in the presence of sucrose but increased in the absence of sucrose, which are parallel to the mRNA levels of αAmy3 and another rice α-amylase gene, αAmy8. By contrast, the levels of OsMYBS2 are higher in the presence than in the absence of sucrose.

Transient expression assays with barley half seeds were used as a system for studying the function of OsMYBS prteins in sugar and hormone regulation in later experiments. To determine whether OsMYBS genes are expressed in barley aleurone cells, total RNA was isolated from barley half seeds and subjected to gel blot analysis using OsMYBS-specific DNAs as probes. All of these OsMYBS genes are expressed in barley aleurone cells in the absence of glucose. The expression levels of OsMYBS1 and OsMYBS3 are suppressed in the presence of glucose or GA, but remain unchanged in the presence of ABA. The expression of OsMYBS2 is enhanced in the presence of glucose, and slightly suppressed by ABA treatment.

3. OsMYBS Proteins Interact Specifically with the TATCCA Element in vitro

To determine whether the three OsMYBS proteins bind specifically to the TATCCA element, they were expressed in E. coli. Interaction between affinity-purified recombinant OsMYBS proteins and five DNA fragments encompassing −171 to −82 region of the αAmy3 SRS was analyzed by gel mobility shift assay. The five DNA fragments, designated F1 through F5, were previously used in gel mobility shift assays for their interaction with nuclear protein extract from rice suspension cells (Lu, et al. (1998) J. Biol. Chem. 273, 10120-10131). F2, which contains the duplicated TATCCA element with some flanking sequence in SRS, was used as the probe for gel mobility shift assays. The three recombinant OsMYBS proteins bound to probe F2, resulting in the formation of low mobility complexes. The interaction between OsMYBS1 or OsMYBS2 and F2 was competed out only by F2 and the DNA fragment containing 6 tandem repeats of the 6-bp TATCCA element but not by 500-fold excess of other DNA fragments. The interaction between OsMYBS3 and F2 was also competed out only by F2; F5, which contains the TATCCA element; and the DNA fragment containing 6 tandem repeats of the 6-bp TATCCA element. A 17-bp DNA fragment containing the TATA box sequence (TATATA), which differs from the TATCCA element by only two nucleotides, did not compete for binding.

To further verify the specificity of binding between OsMYBS proteins and the TATCCA element, a series of site-directed mutations spanning region −119 to −102 that containing the TATCCA tandem repeat were constructed. The wild type (Wt) sequence was used as the probe for gel mobility shift assays. The three recombinant OsMYBS proteins bound to the Wt probe, resulting in the formation of low mobility complexes. Also, the bindings of each of these OsMYBS proteins were completely competed out by unlabeled Wt sequence. The DNA sequence with mutations throughout both repeats (M1) failed to compete, and sequences with either of the repeats replaced (M2 and M3) competed less effectively. Mutating three of the six bases in both of these repeats (M4, M5, and M6) could only slightly compete. These results suggest that all of these OsMYBS proteins bind specifically to two copies of the TATCCA element. However, the binding affinity decreases if only one copy of TATCCA exists.

4. OsMYBS Proteins Interact with the TATCCA Element in vivo

The in vivo binding activity of OsMYBS proteins to the TATCCA element was analyzed using a yeast one-hybrid system. The full-length OsMYBS sequences were individually fused at the C-terminus with the activation domain of the yeast GAL4 transcriptional activator (GAD). The GAD-OsMYBS chimeric gene was then fused downstream of the yeast ADH1 promoter and used as an effector construct. A yeast strain containing a Cyc1 minimal promoter-LacZ fusion reporter construct was then transformed with the effector construct. The presence of GAD alone or together with the GAD-OsMYBS fusion protein did not lead to expression of LacZ.

Eight tandem repeats of the −133 to −82 DNA sequence of αAmy3, designated 8x(TATCCA+F), was fused upstream of the Cyc1 minimal promoter-LacZ coding region and served as a reporter construct. The reporter construct was delivered into yeast first, and the yeast was then transformed with the effector constructs containing the ADH1-GAD-OsMybS fusion gene. The presence of GAD alone increased LacZ expression by 5-fold, indicating that the TATCCA element with flanking sequences slightly enhanced the Cyc1 minimal promoter activity even in the absence of OsMYBS. The presence of GAD-OsMYBS1 and GAD-OsMYBS2 increased LacZ expression by 3- and 5-fold, respectively, compared with LacZ expression in the absence of OsMYBS. In contrast, the presence of OsMYBS3 reduced LacZ expression by 2-fold.

To test whether the flanking sequence of the TATCCA element affects the binding affinity of OsMYBS1 and OsMYBS2, six tandem repeats of the 6-bp TATCCA element, designated 6xTATCCA, were fused upstream of the Cyc1 minimal promoter-LacZ coding region and served as a reporter construct. The reporter construct was delivered into yeast and the yeast was then transformed with the effector construct that contains the ADH1-GAD-OsMYBS fusion gene. Only the presence of GAD-OsMYBS2 increased LacZ expression.

5. OsMYBS1 and OsMYBS2 are Transcriptional Activators

To determine whether OsMYBS is a transcriptional activator, the full-length OsMYBS sequence was fused at the C-terminus of the DNA-binding domain of GAL4 (GBD). The chimeric gene was then fused downstream of the yeast ADH1 promoter and used as an effector construct. A yeast strain hosting the 3xUAS-Cyc1 minimal promoter-lacZ fusion reporter construct was then transformed with the effector construct. The presence of the GBD-OsMybS1 fusion protein increased LacZ expression 8-fold, GBD-OsMYBS2 only slightly increased LacZ expression, and GBD-OsMYBS3 did not increase LacZ expression.

A yeast strain harboring the GAL1 promoter-HIS3 fusion reporter construct was also transformed with the effector construct that contains the ADH1-GBD-OsMYBS fusion gene. The presence of the GBD-OsMYBS1 fusion protein allowed yeast cells to grow well on a medium lacking histidine in the presence of 3-AT. The presence of the GBD-OsMYBS2 fusion protein allowed yeast cells to grow slowly, but the presence of the GBD-OsMYBS3 fusion protein did not allow yeast cells to grow on the selective medium. The above results suggest that OsMYBS1 is a strong transcriptional activator, OsMYBS2 is a weak transcriptional activator, and OsMYBS3 is not a transcriptional activator in yeast.

6. OsMYBS1 and OsMYBS2 Derepress Sugar-repressed Transcription of a Promoter Containing SRS To determine the function of OsMYBS in sugar regulation of α-amylase gene expression in plant cells, the transactivation ability of OsMYBS on SRS fused to the CaMV35S minimal promoter (−46 bp upstream of transcription start site), forming an SRS-CaMV35S chimeric promoter, was analyzed in barley aleurone cells that yield more consistent results than rice protoplasts. The three OsMYBS cDNAs were individually fused downstream of the maize ubiquitin gene (Ubi) promoter, forming Ubi-OsMYBS chimeric genes, which served as effectors. The coding region of the luciferase gene (Luc) was fused downstream of the SRS-CaMV35S chimeric promoter and served as a reporter. The barley half seeds were particle-bombarded simultaneously with the effector and reporter plasmids. The bombarded half seeds were divided into two halves and each half was incubated with 0.3 M glucose or 0.3 M mannitol for 24 h, and luciferase activity was determined. Luciferase activity was higher in the absence of glucose when the half seeds were co-bombarded with the reporter plasmid and plasmid pRS426, an unrelated yeast plasmid with a molecular weight similar to that of the effector plasmid, which was used as a negative control. This result is consistent with our previous finding that the SRS-CaMV35S chimeric promoter was activated in rice protoplasts in the absence of glucose and repressed in the presence of glucose (Lu, et al. (1998) J. Biol. Chem. 273, 10120-10131). When the half seeds were co-bombarded with the reporter and effector plasmids, OsMYBS1 significantly enhanced luciferase activity in the presence of glucose to a level similar to the level in the absence of glucose. OsMYBS1 also enhanced luciferase activity in the absence of glucose, but to a lesser extent. OsMYBS2 enhanced luciferase activity in the presence of glucose, but did not affect the activity in the absence of glucose. OsMYBS3 did not significantly enhance luciferase activity in the presence of glucose and repressed luciferase activity in the absence of glucose. These results indicate that OsMYBS1 and OsMYBS2 function as a strong and weak activator, respectively, and that OsMYBS3 serves as a repressor, for transcription of the promoter containing SRS.

7. OsMYBS1 Derepresses Sugar-repressed Transcription of a Promoter Containing the TATCCA Element with Adjacent Flanking Sequences To determine whether OsMYBS transactivates a promoter containing only the TATCCA element and adjacent flanking sequences, a DNA fragment containing 6 tandem repeats of the −133 to −82 sequence of SRS, designated 6x(TATCCA+F), was fused to the CaMV35S minimal promoter. A plasmid containing the Ubi-OsMYBS construct served as an effector, and Luc cDNA fused downstream of the 6x(TATCCA+F)-CaMV35S promoter served as a reporter. The barley half seeds were co-bombarded with the effector and reporter plasmids. The bombarded half seeds were divided into two halves and each half was incubated with 0.3 M glucose or 0.3 M mannitol for 24 h, and luciferase activity was determined. OsMYBS1 significantly enhanced luciferase activity in the presence of glucose to the same level as in the absence of glucose. Although OsMYBS2 and OsMYBS3 seemed to slightly enhance luciferase expression in the presence of glucose, they significantly suppressed luciferase activity in the absence of glucose. This result indicates that OsMYBS1 activates, while OsMYBS2 and OsMYBS3 repress, transcription of a promoter containing only the TATCCA element and adjacent flanking sequences.

8. OsMYBS Proteins Cooperate with HvMYBGa in Transactivation of a Barley Amy32b Promoter The GARC present in α-amylase gene promoters includes a GARE and the TATCCA element (Gubler and Jacobsen (1992) Plant Cell 4, 1435-1441; Lanahan, et al. (1992) Plant Cell 4, 203-211). HvMYBGa has been shown to bind specifically to GARE in vitro, and to activate transcription of barley high-pI α-amylase and cysteine proteinase gene promoters in the absence of GA in vivo (Gubler, et al. (1995) Plant Cell 7, 1879-1891; Cercós, et al. (1999) Plant J. 19, 107-118). Since the TATCCA element is essential for high-level GA-activated transcription of α-amylase gene promoters (Gubler and Jacobsen (1992) Plant Cell 4, 1435-1441; Lanahan, et al. (1992) Plant Cell 4, 203-211), whether or not the OsMYBS proteins cooperate with HvMYBGa in enhancing transcription of the α-amylase gene promoter was tested. The barley half seeds were co-bombarded with an effector plasmid containing the Ubi-HvMYBGa construct, another effector plasmid containing the Ubi-OsMYBS construct, and the reporter plasmid containing the Amy32b-GUS construct. GUS was expressed only in the presence of GA when no HvMYBGa was present, and overexpression of HvMYBGa significantly enhanced GUS activity in the absence of GA. This result is consistent with other results reported in the literature (Gubler, et al. (1995) Plant Cell 7, 1879-1891; Cercós, et al. (1999) Plant J. 19, 107-118). Interestingly, co-expression of HvMYBGa with OsMYBS1, OsMYBS2, or OsMYBS3 further enhanced GUS activity by approximately 2-3-fold of that with expression of HvMYBGa alone in the absence of GA. These results suggest that the three OsMYBS proteins cooperate with HvMYBGa in transactivation of the barley α-amylase gene promoter.

9. Suppressor of OsMYBS Proteins

Rice embryos were co-bombarded using a standard method with a reporter plasmid p3Luc.18 and an effector construct encoding Ubi fusion protein Ubi-OsMYBS1 or Ubi-OsBZ8. OsBZ8 is a bZIP protein. The bombarded rice embryos were divided into two halves, each half was incubated in the presence or absence of 100 mM glucose for 18 hours. Luciferase assays were then carried out as described above to determine effects of OsBZ8 on the transactivity of OsMYBS1. The results indicate that OsBZ8 completely suppressed the transactivity of OsMYBS1.

Rice embryos were also co-bombarded with a reporter construct T7 containing a modified αAmy8SRS/GARS promoter linked to the CaMV35S minimal promoter-Luc chimeric gene, an effector plasmid containing the Ubi-OsMYB1, and another effector plasmid encoding Ubi-HvMYBGa or AtABI5. AtABI5 is a G-box binding bZIP factor (Finkelstein et al., (2000) Plant Cell 12: 599-609). Luciferase assays were carried out by a standard method. The results indicate that HvMYBGa and AtABI5 increased the ability of OsMYB1 to transactivate the expression of the reported gene by 4-5 and 2-3 fold, respectively.

10. OsMybS1 Forms A Homodimer in Barley Aleurone Cells

In c-Myb, R2 and R3 bind to specific DNA sequences cooperatively. To test the possibility that OsMYBS binds DNA as dimers, homologous and heterologous interactions among OsMYBS proteins were analyzed using a two-hybrid system in barley aleurone cells. The full-length OsMYBS sequences were individually fused at the C-terminus of GAD or GBD. The GAD-OsMYBS and GBD-OsMYBS chimeric genes were fused downstream of the Ubi promoter and used as effector constructs. A DNA fragment containing five tandem repeats of UAS (5×UAS) was fused upstream of the CaMV35S minimal promoter-Luc chimeric gene and used as a reporter construct. The barley half seeds were particle-bombarded simultaneously with two effector plasmids, each containing GAD-OsMYBS and GBD-OsMYBS fusion genes, and the reporter plasmid. The bombarded half seeds were incubated in buffer without glucose for 24 h, and luciferase activity was determined. Coexpression of GBD-OsMYBS1 and GAD-OsMYBS1 significantly enhanced luciferase expression compared with the expression of GBD-OsMYBS1 alone. However, coexpression of GBD-OsMYBS1 and GAD-OsMYBS2 or GAD-OsMYBS3 did not further enhance luciferase activity compared with the expression of GBD-OsMYBS1 alone. Similar experiments with OsMYBS2 and OsMYBS3 showed that the two proteins did not interact homologously or heterologously. To confirm that only OsMYBS1 interact homologously with one another and the three OsMYBS proteins do not interact with each other, the effector and reporter plasmids were reconstructed for expression in yeast. Except that the background level of reporter gene expression in the presence of GBD-OsMYBS1 alone is too high to detect the interactions between GBD-OsMYBS1 and GAD-OsMYBS proteins, similar results were obtained with the yeast two-hybrid experiments. These results suggest that only OsMYBS1 forms homodimer under these experimental conditions.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An isolated nucleic acid comprising the sequence of SEQ ID NO:1.

2. The nucleic acid of claim 1, wherein the nucleic acid encodes a polypeptide containing SEQ ID NO:7.

3. An isolated cell comprising the nucleic acid of claim 2.

4. A transgenic plant that contains the nucleic acid of claim 2.

5. The transgenic plant of claim 4, wherein the plant is a monocot plant.

6. The transgenic plant of claim 5, wherein the plant is a cereal plant.

7. The transgenic plant of claim 6, wherein the plant is rice.

8. The transgenic plant of claim 6, wherein the plant is barley.

9. A method of expressing a transcript in an isolated cell, the method comprising:

introducing a vector into an isolated cell, the vector comprising a nucleic acid encoding a polypeptide containing the amino acid sequence of SEQ ID NO:7, and expressing the transcript in the cell.

10. The method of claim 9, wherein the sequence of the polypeptide consists of SEQ ID NO:7.

11. The isolated nucleic acid of claim 1, wherein the amino acid sequence of the encoded polypeptide consists of SEQ ID NO: 7.

* * * * *